United States Patent [19]

Kawakami et al.

[11] Patent Number: 4,802,058

[45] Date of Patent: Jan. 31, 1989

[54] NOVEL METHOD FOR REFINING ELECTRICAL INSULATING OIL

[75] Inventors: Shigenobu Kawakami, Ichikawa; Keiji Endo, Yokosuka; Hideyuki Dohi, Yokohama; Atsushi Sato, Tokyo, all of Japan

[73] Assignee: Nippon Petrochemicals Company, Limited, Japan

[21] Appl. No.: 165,728

[22] Filed: Mar. 9, 1988

[30] Foreign Application Priority Data

Mar. 11, 1987 [JP] Japan .................................. 62-55865

[51] Int. Cl.[4] .......................... H01G 4/22; C10L 1/10; H01B 3/22; C07C 15/12

[52] U.S. Cl. .................................... 361/315; 252/567; 208/14; 585/320

[58] Field of Search .................................... 174/17 LF; 361/314–319; 208/14; 585/6.3, 436, 320; 252/567, 570, 578, 579

[56] References Cited

U.S. PATENT DOCUMENTS

| | | | |
|---|---|---|---|
| 4,108,788 | 8/1978 | Schulz et al. | 585/6.3 X |
| 4,115,464 | 9/1978 | Bartek et al. | 585/436 |
| 4,365,103 | 12/1982 | Chang et al. | 585/320 |
| 4,591,948 | 5/1986 | Sato et al. | 252/567 X |
| 4,681,980 | 7/1987 | Sato et al. | 585/436 X |
| 4,755,275 | 7/1988 | Sato et al. | 252/570 X |

*Primary Examiner*—Donald A. Griffin
*Attorney, Agent, or Firm*—Scully, Scott, Murphy & Presser

[57] ABSTRACT

The present invention relates to a method for refining an electrical insulating oil by refining a heavy by-product oil obtained in the preparation of ethylbenzene or ethyltoluene. The method comprises distilling off the lighter components from the by-product oil, then dehydrogenating, distilling and hydrogenating.

5 Claims, No Drawings

NOVEL METHOD FOR REFINING ELECTRICAL INSULATING OIL

BACKGROUND OF THE INVENTION (1) Field of the Invention

The present invention relates to a method for refining an electrical insulating oil and, more particularly, to a method for refining an electrical insulating oil by refining a heavy by-product oil produced in the preparation of ethylbenzene or ethyltoluene by alkylating benzene or toluene with ethylene in the presence of an alkylating catalyst, thereby producing an electrical insulating oil having excellent electrical characteristics.

(2) Description of the Prior Art

Production of a heavy by-product oil containing 1,1-diphenylethane in the preparation of ethylbenzene by introducing ethylene into benzene in the presence of an alkylating catalyst is known as described in, e.g., U.S. Pat. No. 4,111,825. This prior art reports that such a by-product oil is useful as an electrical insulating oil. The present inventors found that excellent electrical characteristics of a capacitor could not be obtained even if a fraction of 1,1-diphenylethane having a boiling point of 265 to 285° C. and contained in the by-product oil was recovered and was impregnated in a polypropylene film to prepare an oil-filled capacitor due to impurities inevitably contained in the fraction. According to an analysis of the present inventors, the fraction contained alkyldecalins, cyclohexylethylbenzene, ethylcyclohexylbenzene, and the like in addition to 1,1-diphenylethane. These impurities tend to undesirably swell the polypropylene film. The fraction consists of a low aromatic group which tends to undesirably degrade electrical characteristics. These impurities have boiling points close to that of 1,1-diphenylethane and cannot be separated by a simple distillation method. If these impurities are eliminated and the oil can be refined by a method replacing distillation, an electrical insulating oil having excellent electrical characteristics can be provided.

U.S. Pat. No. 4,681,980 proposes as an electrical insulating oil an aromatic olefin-containing fraction produced by dehydrogenating a diarylalkane-containing fraction as a by-product oil in the preparation of ethylbenzene. Hydrogenation is not performed although dehydrogenation is performed in the above patent. Therefore, the method described in U.S. Pat. No. 4,681,980 is not a method for refining the diarylethane-containing fraction.

BRIEF SUMMARY OF THE INVENTION

It is an object of the present invention to provide an electrical insulating oil excellent in electrical characteristics and oxidation stability and containing a small number of components which adversely affect the electrical characteristics by refining a fraction under specific conditions.

The present invention provides a method of refining an electrical insulating oil, comprising the steps (I) to (V) as follows:

(I) a step of alkylating benzene or toluene with ethylene in the presence of an alkylating catalyst to produce a heavy oil containing diarylethanes;

(II) a step of distilling the heavy oil to recover a diarylethane-containing fraction mainly consisting of components having boiling points lower than those of the corresponding diarylethylenes as a dehydrogenated product of the diarylethanes;

(III) a step of dehydrogenating the diarylethane-containing fraction with a dehydrogenation catalyst and converting at least part of the diarylethanes in the fraction into diarylethylenes, thereby preparing a diarylethylene-containing fraction;

(IV) a step of distilling a light fraction lighter than the diarylethylenes from the diarylethylene-containing fraction, thereby increasing the concentration of the diarylethylenes in the fraction; and (V) a step of hydrogenating the diarylethylene-containing fraction having the increased concentration of diarylethylenes in the presence of a hydrogenation catalyst under conditions which substantially inhibit nucleus hydrogenation, thereby converting at least part of the diarylethylenes in the fraction into diarylethanes.

DETAILED DESCRIPTION OF THE INVENTION

The present invention will be described in detail below.

Benzene or toluene is alkylated in the presence of an alkylating catalyst to prepare ethylbenzene or ethyltoluene as a petrochemical material for the production of styrenes in a large-scale industrial line.

The heavy oil containing a diarylethane in step (I) is a by-product oil produced in the preparation process of the above-mentioned alkylation.

More specifically, alkylation is generally performed by liquid- or gaseous-phase alkylation. In liquid-phase alkylation, a Friedel-Crafts catalyst (e.g., aluminum chloride) or an alkylating catalyst (e.g., sulfuric acid, toluenesulfonic acid, or Bronsted acid such as hydrofluoride) is used. The aluminum chloride alkylation catalyst is preferable because the effect of the present invention is expected in great deal in the case that the aluminum chloride alkylation catalyst is used. In gaseous-phase alkylation, a catalyst prepared by causing a solid acid such as synthetic zeolite (e.g., ZSM-5) or a phosphoric acid carried on a proper carrier is used as an alkylating catalyst. A reaction temperature falls within the range of 20 to 180° C. in liquid-phase alkylation and 250 to 450° C. in gaseous-phase alkylation.

After alkylation of benzene or toluene with ethylene, in addition to the nonreacted benzene or toluene as well as ethylbenzene or ethyltoluene as an objective product, an alkylated product containing a heavier oil and a polyalkylbenzene (e.g., polyethylbenzene or polyethyltoluene) excluding monoethylated products are obtained. The catalyst is eliminated from the alkylated product as needed. Also, the alkylated product is neutralized or washed with water. Thereafter, the nonreacted benzene or toluene, ethylbenzene or ethyltoluene as the objective product, and most of polyethylbenzene and polyethyltoluene are distilled by vacuum or normal pressure distillation from the alkylated product, thereby obtaining a heavy oil. There can be conducted, if necessary, a refining treatment according to the method such as the one described in U.S. Pat. No. 4,108,788. The resultant heavy oil contains a relatively large amount of diarylethanes such as 1,1-diphenylethane, and 1-phenyl-1-ethylphenylethane.

In step (II) of the present invention, a fraction containing a diarylethane is recovered from above-mentioned heavy oil containing the diarylethane by distillation. The recovered fraction contains the diarylethane. In this case, the heavy oil mainly contains components having boiling points lower than that of a corresponding diarylethylene as a dehydrogenated product of the diarylethane. The above distillation is normally performed by reduced pressure distillation.

In general, a diarylethane has a boiling point lower than that of the corresponding diarylethylene as a dehydrogenated product. For example, 1,1-diphenylethane has a boiling point of 272.6° C. (atmospheric pressure basis), and the corresponding diphenylethylene as a dehydrogenated product has a boiling point of 277.1° C. In other words, a diarylethane is dehydrogenated and converted into the corresponding diarylethylene having a higher boiling point.

In step (II), it is important to perform distillation so as to substantially exclude components having boiling points higher than the diarylethylene produced in step (III). Then, a fraction containing a small amount of impurities can be obtained.

As described above, the heavy oil contains components which cannot be eliminated by simple distillation. For example, 1,1-diphenylethane is considered. High-precision normal distillation in vacuum allows recovery of 75 to 85% of 1,1-diphenylethane under the normal condition. An increase in concentration of 1,1-diphenylethane higher than that is not preferable in favor of distillation efficiency and an economical advantage. It is also impossible to recover a fraction containing 100% of 1,1-diphenylethane only by distillation.

The fraction containing a diarylethane recovered in step (II) is dehydrogenated in the presence of a dehydrogenating metal oxide catalyst in step (III), and at least part of the diarylethane in the fraction is converted into a diarylethylene.

Due to the reaction equilibrium, the dehydrogenation progresses more when a reaction pressure is lower. The reaction progresses more at a higher temperature since the dehydrogenation reaction is a strongly endothermic reaction. Therefore, the reaction temperature is selected to fall within the range of 500 to 700° C. and, preferably 550 to 650° C. If the reaction temperature is lower than 500° C., the dehydrogenation reaction cannot progress. However, if the reaction temperature exceeds 700° C., a side reaction such as decomposition undesirably occurs. A reaction pressure is selected to fall within the range of a reduced pressure to 5 $kg/cm^2$ and, preferably a reduced pressure to about 3 $kg/cm^2$. A typical heating medium is excess steam.

Examples of the dehydrogenating catalyst are a chromia-alumina catalyst and an iron oxide catalyst. The dehydrogenating catalyst can be used together with as an assistant catalyst an oxide of potassium carbonate, chrominum, cerium, molybdenum, or vanadium.

At least part of the diarylethane in the fraction can be converted into a diarylethylene by the dehydrogenation reaction in step (III). 30% and preferably 50% of the diarylethane must be converted into a diarylethylene. If the convertion percentage is lower than the value described above, the effect of the present invention cannot be obtained.

By the dehydrogenation reaction in step (III), the alkyldecalins which adversely affect the electrical and other characteristics are converted into alkylnaphthalenes, and cyclohexylethylbenzene and ethylcyclohexylbenzene are converted into ethylbiphenyls. The resultant products are highly aromatic hydrocarbons having higher boiling points. These compounds have higher boiling points and may be contained in the final fraction in the step of the present invention. However, since the residual compounds are highly aromatic hydrocarbons, the properties of the electrical insulating oil can be further improved.

Light components contained in the dehydrogenated fraction are distilled in step (IV). This distillation is performed by high-precision normal or vacuum distillation. The light components to be distilled are components having boiling points lower than that (converted at the normal pressure) of the resultant diarylethylene.

Since the fraction lighter than the diarylethylene is distilled in step (IV), the concentration of the diarylethylene in the fraction can be increased. The fraction obtained by distillation in step (IV) contains 70 wt % or more of the diarylethylene and preferably 75 wt % or more of the diarylethylene. If the concentration is less than 70 wt %, the effect of the present invention cannot be obtained.

The fraction containing the diarylethylene recovered by distillation in step (IV) is hydrogenated in the presence of a hydrogenating catalyst under conditions which substantially inhibit nucleus hydrogenation. Therefore, at least part of the diarylethylene in the fraction is converted into the diarylethane, of which aromatic nucleus is not hydrogenated.

A hydrogenating catalyst may be: a catalyst prepared by carrying nickel, cobalt, molybdenum, or a combination thereof on a carrier such as alumina or silica-alumina; or a noble metal catalyst prepared by carrying a noble metal such as palladium, rhodium, or platinum on an active carbon. Of these catalysts, a noble metal catalyst carrying palladium or the like is preferable since it is free from substantial nucleus hydrogenation of the aromatic group nucleus.

A reaction temperature preferably falls within the range of 50 to 150° C. Hydrogenation at a temperature exceeding 150° C. does not present any practical problems. However, a temperature exceeding 150° C. need not be used. A hydrogen pressure is preferably 1 to 50 $kg/cm^2$. A reaction tends not to occur at a pressure lower than the lower limit of the above range. However, if the pressure exceeds 50 $kg/cm^2$, a side reaction tends to undesirably occur. The amount of catalyst is preferably 0.5 to 5 wt % with respect to the total content of the fraction. A reaction system may be of a flow or batch type. A reaction time in the flow type reaction system is LTSV0.1 to 10; and a reaction time in the batch type reaction system is 0.5 to 2 hours. The reacted fraction can be used as an electrical insulating oil directly or after the catalyst is removed from the fraction. However, when light components are produced by hydrogenation, these components must be removed by distillation as needed.

In addition, distillation can be performed again to control the boiling point to a predetermined temperature.

In the hydrogenation described above, the diarylethylene need not be entirely converted into the diarylethane. A predetermined amount of diarylethylene may be left unconverted in consideration of the oxidation stability of the fraction prepared by hydrogenation and other properties.

The electrical insulating oil prepared by the method of the present invention is suitably applied as a capacitor oil, a cable oil and an oil impregnated in an oil-filled electrical appliance (e.g., an oil-filled capacitor and an oil-filled cable) partially using a plastic material as an insulating material or a dielectric material. Examples of the insulating plastic material are polyester, polyvinylidene fluoride, and a polyolefin (e.g., polypropylene and polyethylene). An oil-filled capacitor is prepared such that a metal film as a conductor such as aluminum and a plastic film are wound and are impregnated with the electrical insulating oil. Alternatively, a metallized plastic film having a metal deposition layer as a conductive layer of aluminum or zinc is wound together with a plastic film or insulating paper, and the resultant structure is impregnated with the electrically insulating oil. An oil-filled cable is prepared such that a paper-plastic laminated film or an insulating material such as a plastic unwoven fabric is wound around a conductive material of copper or the like, and the resultant structure is impregnated with the electrical insulating oil.

When the oil of the present invention is used as an electrical insulating oil, a known electrical insulating oil such as phenylxylylethane, alkylbiphenyl, or alkylnaphthalene can be added thereto in a proper amount. Impurities in the fraction containing a diarylethane obtained by a specific alkylation process, which adversely affect the electrical properties and are not always suitable for preparing an oil-filled electrical appliance (e.g. an oil-filled capacitor) using a plastic film, can be greatly reduced by the refining method of the present invention. As a result, the properties of the fraction can be improved. Therefore, the oil-filled capacitor prepared by using the electrical insulating oil refined by the method of the present invention is excellent in corona discharge characteristics and low-temperature characteristics. Oxidation stability and thermal stability of the capacitor can be improved by hydrogenation.

The present invention will be described in detail by way of its example.

EXAMPLE

Step (I): Alkylation of Benzene with Ethylene

In the process for preparing ethylbenzene such that benzene was alkylated by ethylene by a liquid-phase alkylation method using an aluminum chloride catalyst, an alkylated product was obtained. This alkylated product contained 43.0 wt % of nonreacted benzene, 11.8 wt % of ethylbenzene, 18.3 wt % of polyethylbenzene, and 7.6 wt % of a heavy oil containing diarylethanes. The nonreacted benzene, the ethylbenzene, and polyethylbenzene were distilled from the alkylated product. The heavy oil as its residue was a viscous black material containing a tar-like material.

Step (II): Distillation

The heavy oil was distilled by vacuum distillation to recover a fraction having a flow temperature range of 265 to 285° C. (converted at the normal pressure). The composition of the resultant fraction was as given below. This fraction mainly contained components having boiling points lower than that (converted at the normal pressure) of 1,1-diphenylethylene and is defined as fraction 1.

| Component | wt % |
|---|---|
| 1,1-diphenylethane | 77.8 |
| Alkyldecalins<br>Cyclohexylethylbenzene<br>Ethylcyclohexylbenzene | 15.7 |
| Others | 6.5 |
| total: | 100.0 |

Step (III): Dehydrogenation Reaction

The above fraction was dehydrogenated under the following conditions:

| | |
|---|---|
| Catalyst: | Nissan Girdler G-64C (tradename) (an iron oxide catalyst with potassium carbonate and chromium oxide as promoters) |
| Temperature: | 600° C. |
| LHSV: | 2.0 |
| Water/Hydrocarbon | 2.0 |

The reacted solution was analyzed and analyst results are obtained as follows:

| | |
|---|---|
| Light components | 1.0% |
| 1,1-diphenylethane | 13.4% |
| 1,1-diphenylethylene | 64.4% |
| Alkyldecalins<br>Cyclohexylethylbenzene<br>Ethylcyclohexylbenzene | 6.9% |
| Ethylbiphenyl | 5.3% |
| Others | 9.0% |

Step (IV): Distillation

The above reacted solution was distilled by vacuum distillation, the light components produced in the dehydrogenation reaction were removed, and the concentration of 1,1-diphenylethylene was set to be 80%. The recovered fraction had the following composition:

| | |
|---|---|
| 1,1-diphenylethane | 8.5% |
| 1,1-diphenylethylene | 80.0% |
| Alkyldecalins<br>Cyclohexylethylbenzene<br>Ethylcyclohexylbenzene | 4.6% |
| Ethylbiphenyl | 4.4% |
| Others | 2.5% |

Step (V): Hydrogenation

The above fraction was hydrogenated. The reaction was performed using a 1-liter autoclave.

500 milliliters of the above fraction and 5 g of Pd/c as a catalyst were poured in the autoclave and were reacted at a temperature of 70° C. and a hydrogen pressure of 15 kg/cm$^2$ for 2 hours. After the catalyst was removed, the composition of the reacted solution was analyzed as follows. This fraction is defined as fraction 2.

| | |
|---|---|
| 1,1-diphenylethane | 88.5% |
| Alkyldecalins<br>Cyclohexylethylbenzene<br>Ethylcyclohexylbenzene | 4.6% |
| Ethylbiphenyl | 4.4% |
| Others | 2.5% |

(Compatibility with Polypropylene Film)

Polypropylene films having a predetermined shape and a thickness of 14 microns were dipped in fractions 1 and 2, respectively, at 80° C. for 72 hours. The films were then removed from fractions 1 and 2, and swelling indices of the films before and after dipping were measured, and the results are summarized below:

Fraction 1: 9.1%

Fraction 2: 7.0%

When the percentage is small, i.e., when the film swelling index is small, the film was not so swelled and provided excellent dimensional stability. Therefore, fraction 2 has better compatibility with the polypropylene film.

(Measurement of Corona Starting Voltage (CSV) and Corona Ending Voltage (CEV))

Two polypropylene films each having a thickness of 14 microns were used as a dielectric material, and an aluminum film was wound and stacked to constitute electrodes according to a conventional technique, thereby preparing oil-filled capacitor models.

These capacitor models were impregnated with the respective fractions in a vacuum to obtain 0.4-μF oil-filled capacitors.

The corona starting and ending voltages (CSV and CEV) of these 0.4-μF oil-filled capacitors at room temperature were measured, and measurement results are summarized in Table 1.

(Life Test of Capacitor)

Two polypropylene films each having a thickness of 14 microns were used as a dielectric material, and an aluminum film was wound and stacked to constitute electrodes according to a conventional technique, thereby preparing oil-filled capacitor models.

These capacitor models were impregnated with the respective fractions in a vacuum to obtain 0.4-μF oil-filled capacitors.

A predetermined AC voltage was applied to these capacitors at room temperature and durations for causing breakdown of these capacitors were measured to obtain their service life. In this case, the potential was increased from a potential gradient of 80 V/μ at a rate of 10 V/μ every 48 hours, and the number of capacitors subjected to breakdown was counted. The number of capacitors at the start of measurement was 10 for each fraction. Test results are summarized in Table 2.

TABLE 1

| Item | Fraction 1 | Fraction 2 |
|---|---|---|
| CSV (V/μ) | 98 | 110 |
| CEV (V/μ) | 72 | 84 |

TABLE 2

| | Number of Capacitors Subjected Breakdown | |
|---|---|---|
| Potential Gradient (V/μ) | Fraction 1 | Fraction 2 |
| 80 | — | — |
| 90 | 1 | — |
| 100 | 6 | — |
| 110 | 3 | — |
| 120 | — | — |
| 130 | — | 2 |
| 140 | — | 8 |

What is claimed is:

1. A method of refining an electrical insulating oil, comprising steps of:

(I) alkylating benzene or toluene with ethylene in the presence of an alkylating catalyst to produce a heavy oil containing diarylethanes;

(II) distillating the heavy oil to recover a fraction containing diarylethanes, said fraction mainly consisting of components having boiling points lower than those of the corresponding diarylethylenes as a dehydrogenated product of said diarylethanes;

(III) dehydrogenating the fraction containing the diarylethanes by a hydrogenation catalyst to convert at least part of the diarylethanes in the fraction into diarylethylenes, thereby preparing a fraction containing the diarylethylenes;

(IV) distilling components lighter than the diarylethylenes from the fraction containing the diarylethylenes to increase the concentration of the diarylethylenes; and (V) hydrogenating the fraction containing the diarylethylenes having the increased concentration in the presence of a hydrogenation catalyst under conditions which substantially inhibit nucleus hydrogenation, thereby converting at least part of the diarylethylenes in the fraction into diarylethanes.

2. A method according to claim 1, wherein the diarylethane is 1,1-diphenylethane and the diarylethylene is 1,1-diphenylethylene.

3. A method according to claim 1, wherein the alkylating catalyst in the step (I) is a Friedel-Crafts catalyst.

4. A method according to claim 3, wherein the Friedel-Crafts catalyst is aluminum chloride.

5. An electrical appliance impregnated or filled with the electrical insulating oil which is refined by the method according to claim 1.

* * * * *